United States Patent [19]

Kang

[11] 4,325,884

[45] Apr. 20, 1982

[54] METHOD FOR THE PREPARATION OF BIS($p$-AMINOBENZOATO) COBALT

[75] Inventor: Jung W. Kang, Clinton, Ohio

[73] Assignee: The Firestone Tire & Rubber Company, Akron, Ohio

[21] Appl. No.: 163,463

[22] Filed: Jun. 27, 1980

[51] Int. Cl.³ ............................................. C07F 15/06
[52] U.S. Cl. .............................. 260/439 R; 260/429 J
[58] Field of Search ......................... 260/439 R, 429 J

[56] References Cited

U.S. PATENT DOCUMENTS 4,060,535 11/1977 Cinco ................................. 260/414

OTHER PUBLICATIONS

Inomata et al., Bulletin of the Chemical Society of Japan, vol. 46, pp. 1148–1154, (1973).

Primary Examiner—Helen M. S. Sneed

[57] ABSTRACT

A method for the preparation of anhydrous bis($p$-aminobenzoato) cobalt includes the steps of forming a suspension of cobalt hydroxide and $p$-aminobenzoic acid in water, heating the suspension with constant stirring to form a solid product, separating, washing, drying and dehydrating the solid to yield the anhydrous product.

2 Claims, No Drawings

METHOD FOR THE PREPARATION OF BIS(p-AMINOBENZOATO) COBALT

TECHNICAL FIELD

The present invention is directed to a novel method for the direct preparation of anhydrous bis(p-aminobenzoato) cobalt from the reaction of p-aminobenzoic acid and cobalt hydroxide in aqueous solution. The anhydrous cobalt chelate compound that is formed is useful as an adhesion promoter for sulfur-vulcanizable rubber-to-metal bonds as are encountered in steel-reinforced rubber skim stock compositions used in the manufacture of tires, conveyor belts, hoses and the like. The steel wire or cable can be brass or zinc-plated or unplated, i.e., bright steel.

BACKGROUND ART

Cobalt containing compounds have heretofore been compounded with vulcanizable rubber skim stocks to promote adhesion of the latter to metal. A typical method for improving adhesion is set forth in U.S. Pat. No. 3,897,583 which is directed toward the adhesion of metal to rubber by incorporating a cobalt salt in a rubber stock which contains an adhesive resin forming system based on a methylene donor which is a methylolated nitroalkane in combination with a resorcinol type methylene acceptor. Cobalt salts disclosed include those of aliphatic or alicyclic carboxylic acids having 6–30 carbon atoms.

Similarly, U.S. Pat. No. 3,903,026 discloses a rubber composition containing cobalt carboxylate and magnesium oxide to improve the adhesion between the rubber and zinc or zinc alloy plated steel.

And, U.S. Pat. No. 3,936,536 discloses the method of adhering rubber to metal by coating the metal with rubber containing a small amount of $Co(NH_3)_2.Cl_2$.

Turning from the art of metal adhesion to that of metallic salts, U.S. Pat. No. 4,060,535 discloses a process for producing metal salts of organic acids by vigorously agitating a mixture of appropriate amounts of the metal oxide, hydroxide or carbonate and the organic acid in water. Among the metals recited is cobalt and among the organic acids is p-aminobenzoic acid. From the examples provided by the patentee, however, it is clear that a true salt was formed and not a chelate structure. Moreover, the metal salt contains up to about 8% by weight of water and up to 1% by weight of free acid. The patent contains no reference to the use of the metal salt as an adhesion promoter and, in fact, would not be useful as such inasmuch as presence of any acid would be likely to lengthen the cure time of the rubber skim stock and could also effect weaker tensile strengths of the product.

Thus, none of these patents discloses a method for the preparation of anhydrous cobalt chelates much less suggests that the chelate could be added to vulcanizable rubber skim stocks as an adhesion promoter.

DISCLOSURE OF INVENTION

It is therefore an object of the present invention to provide a novel method for the preparation of bis(p-aminobenzoato) cobalt that is substantially devoid of free acid.

It is another object of the present invention to provide a method for the preparation of anhydrous bis(p-aminobenzoato) cobalt from the reaction of p-aminobenzoic acid and cobalt hydroxide in aqueous solution.

It is yet another object of the present invention to provide a method for the preparation of an anhydrous chelate of cobalt and p-aminobenzoic acid that can be added to rubber skim stock to improve the adhesion thereof to metallic reinforcements such as steel and brase-plated or zinc-plated steel.

These and other objects, together with the advantages thereof over known methods, which shall become apparent from the specification which follows, are accomplished by the invention as hereinafter described and claimed.

Practice of the present invention includes the steps of forming a suspension of cobalt hydroxide and p-aminobenzoic acid in water, heating the suspension with constant stirring to form a solid product, separating, washing and drying the solid and dehydrating the solid to yield bis(p-aminobenzoato) cobalt. The steps of the preferred method set forth herein can also be applied to other chelating metals and amino acids other than p-aminobenzoic acid.

PREFERRED MODE FOR CARRYING OUT THE INVENTION

According to the method set forth herein, anhydrous bis(p-aminobenzoato) cobalt can be prepared directly from the reaction of p-aminobenzoic acid and cobalt hydroxide in aqueous solution. Although many amino acid chelates of metals such as cobalt, nickel, palladium and cadmium are known, it has not been possible heretofore to prepare an anhydrous chelate of these components that would have utility as an adhesion promoter between rubber skim stock compositions and metallic reinforcement.

The metal component found to be most useful as an adhesion promoter is cobalt, although in the practice of the method herein, other metals such as nickel, palladium, cadmium, copper, calcium, barium, zinc and the like could be substituted if a particular chelate compound thereof were desired. The cobalt is preferably added as the hydroxide salt and the molar amount thereof compared to the molar amount of p-aminobenzoic acid is in the ratio of about 1:2.

Similarly, although the preferred amino acid employed is p-aminobenzoic acid, other amino acids can be employed, having the general formula p-R—NHC$_6$H$_4$COOH wherein R is an aliphatic group such as $CH_3$, $CH_3CH_2$ or $CH_3CO$ or an aromatic group such as $C_6H_5$ or $C_6H_5CO$, if a particular chelate compound other than bis(p-aminobenzoato) cobalt were desired.

The method involves the preparation of an aqueous suspension of the p-aminobenzoic acid and cobalt hydroxide. The suspension, stirred constantly for a period of time of from about one to two hours, is heated at a temperature of from about 25° C. to 100° C. with 75° to 80° C. being preferred. At the end of the stirring and heating phase, the solid product formed is cooled, washed and dried. It is subsequently dehydrated under vacuum at a temperature of about 120° C. to 135° C.

In the two examples which follow, a typical synthesis of anhydrous bis(p-aminobenzoato) cobalt is described.

EXAMPLE I

A suspension of p-aminobenzoic acid (137 g, 1 mole) and cobalt hydroxide (47 g, 0.5 mole) in 1500 ml of distilled water was heated at 75° C. with stirring for one hour during which time a pink-beige solid was formed.

After cooling, the precipitate was collected on a filter, washed with a small amount of distilled water and dried in air. Yield was 157 g. The reddish filtrate was concentrated to a half volume of solvent and was allowed to stand at room temperature to yield 24 g of bis(p-aminobenzoato)Co.4H$_2$O as pink crystals.

The dehydration of the crystals was carried out at about 120° C. under vacuum to give anhydrous bis(p-aminobenzoato)Co as a dark purple crystalline solid. The thermogravimetric analysis (TGA) of anhydrous bis(p-aminobenzoato)Co showed that this complex was stable up to 324° C. (m.p. 324° C. dec.). It also showed 18% of weight loss occurred between 97° to 125° C. which indicated a loss of four moles of water from the hydrated compound bis(p-aminobenzoato)Co.4H$_2$O.

Analysis of the hydrated compound, C$_{14}$H$_{12}$N$_2$O$_4$·Co.4H$_2$O, revealed 13.68% by weight of Co against a calculated amount of 14.64%. Analysis of the anhydrous compound, C$_{14}$H$_{12}$N$_2$O$_4$Co, revealed 16.69% by weight of Co against a calculated amount of 17.78%.

EXAMPLE II

A suspension of p-aminobenzoic acid (137 g, 1 mole) and cobalt hydroxide (47 g, 0.5 mole) in 600 ml of distilled water was heated at 80° C. with vigorous stirring for two hours. The product obtained was dried at 135° C. under vacuum for 18 hours. Yield was 153 g of bis(p-aminobenzoato)Co (m.p. 324° C. dec.). Analysis of the anhydrous compound C$_{14}$H$_{12}$N$_2$O$_4$, revealed 17.54% by weight of Co against a calculated amount of 17.78%.

The anhydrous products of Examples I and II were analyzed on a Beckman Spectrophotometer, Model IR4, in potassium bromide solvent which indicated that an amine group was coordinated to a cobalt ion and that a carboxyl ion was chemically bonded to a cobalt ion. Although the exact structure cannot be explained, it is believed that after the water has been removed from the cobalt compound, a complex is formed in the foregoing manner wherein carboxyl ions and cobalt ions bond in head-to-tails fashion with coordination of amine groups from one molecule or an adjacent molecule occurring with the cobalt ion.

Irrespective of the actual structure, the anhydrous cobalt chelate has utility as an adhesion promoter when compounded with rubber skim stocks in an amount of from about 0.5 to about 10 parts by weight per hundred parts of rubber. It is believed that improved adhesion and adhesion retention is in part due to the lack of free p-aminobenzoic acid and the lack of water in the chelate product.

As stated hereinabove, anhydrous bis(p-aminobenzoato) cobalt can be added to rubber skim stocks to improve the adhesion properties thereof with metallic reinforcements. When such skim stocks are used in steel cord tire construction, for example, it is extremely important, both in new tire construction and retread or repair operations, that the bond between the rubber ply stock and the wire fabric be as flexible and as strong as possible for efficient use under operation conditions; this is especially important in the case of truck tires which are subjected to high loads and speeds with consequent heat buildup due to the rapid flexing of the plies.

Such rubber skim stocks can also be utilized in, for example, metal-rubber articles such as motor mounts, cutless bearings, torsilastic springs, power belts, printing rolls, metal wire reinforced or braided hose, electrical deicers, shoe heels, and wherever it is desired to secure rubber to plated or unplated metal to provide a flexible and strong bond between the same.

Acceptable results would be achieved by employing either coated or bright (unplated) steel wire. The wire coating can be, for example, brass plated wire, i.e., 70% Cu, 30% Zn, or zinc plated. The wire can be in the form of a strand, mat, web, ply or braid.

The skim stock containing anhydrous bis(p-aminobenzoato) cobalt can be applied by use of calendering means, spray means or other known application techniques. Areas of significant utility include, but are not limited to, radiator hose, pneumatic tires, air ride springs, metal reinforced products such as rubber bumpers and sporting goods grips such as golf club handles; in each of these representative areas of utility, the skim stock composition can be used to increase adhesion and adhesion retention properties between metal and rubber, including use in operation when bright steel surfaces are present.

A more detailed discussion regarding adhesion and adhesion retention properties between rubber skim stocks and metallic reinforcement can be obtained by referring to copending application Ser. No. 965,451, filed Nov. 30, 1978 in the name of Ravagnani, et al, and commonly owned by the Assignee of record herein.

Thus, it can be seen that the disclosed invention carries out the objects set forth hereinabove. As will be apparent to those skilled in the art, other chelating metals can be employed in lieu of cobalt such as nickel, zinc, copper, calcium, barium, cadmium or palladium and amino acids other than p-aminobenzoic acid such as N-methyl-p-aminobenzoic acid or N-phenyl-p-aminobenzoic acid can be selected, depending upon the specific compound desired and therefore the subject invention is not to be limited by the examples set forth herein. By following the method set forth herein, anhydrous bis(p-aminobenzoato) cobalt can be directly prepared in good yield and devoid of free acid. It is believed that the preparation and use of the anhydrous cobalt chelate as well as other chelate compounds, prepared according to the preferred method of the invention can be determined without departing from the spirit of the invention herein disclosed and described. Moreover, the scope of the invention shall include all modifications and variations that fall within the scope of the attached claims.

I claim:

1. A method for the preparation of anhydrous bis(p-aminobenzoato) cobalt comprising the steps of sequentially:
    forming a suspension of cobalt hydroxide and p-aminobenzoic acid in water;
    heating said suspension with stirring for a period of time of from 0.5 to about 10 hours at a temperature of from about 25° C. to about 100° C. to form a solid product;
    separating said solid product from the water; and,
    dehydrating said solid product in a vacuum at a temperature from about 120° C. to about 135° C. until such time as the color of said product becomes purple, indicating the completion of chelation.

2. A method for the preparation of anhydrous bis(p-aminobenzoato) cobalt, as set forth in claim 1, wherein the molar ratio of cobalt hydroxide to p-aminobenzoic acid added to form said suspension is approximately 1:2.

* * * * *